United States Patent [19]
Gsell et al.

[11] Patent Number: 5,540,841
[45] Date of Patent: Jul. 30, 1996

[54] CARDIOPLEGIA FILTER AND METHOD FOR PROCESSING CARDIOPLEGIA FLUID

[75] Inventors: Thomas C. Gsell, Glen Cove; Thomas J. Bormann, Melville; Vlado I. Matkovich; Frank R. Pascale, both of Glen Cove, all of N.Y.

[73] Assignee: Pall Corporation, East Hills, N.Y.

[21] Appl. No.: 95,595

[22] Filed: Jul. 26, 1993

[51] Int. Cl.⁶ .......................... B01D 37/00; B01D 36/00; A61M 37/00
[52] U.S. Cl. .................. 210/645; 210/195.1; 210/252; 210/254; 210/295; 210/435; 210/446; 210/493.1; 210/493.5; 210/497.01; 210/767; 210/805; 210/806; 604/4; 604/5; 604/56; 604/113
[58] Field of Search .................................. 210/645, 767, 210/865, 195.1, 195.2, 252, 295, 435, 446, 455, 496, 493.1, 493.5, 806, 497.01, 499, 254; 422/101, 44, 45, 46; 436/177; 604/4, 5, 6, 56, 113; 607/106; 128/DIG. 3

[56] References Cited

U.S. PATENT DOCUMENTS

| | | | |
|---|---|---|---|
| 4,416,280 | 11/1983 | Carpenter et al. | 607/106 |
| 4,568,330 | 2/1986 | Kujawski et al. | 604/4 |
| 4,572,724 | 2/1986 | Rosenberg et al. | 210/436 |
| 4,662,906 | 5/1987 | Matkovich et al. | 210/436 |
| 4,743,371 | 5/1988 | Servas et al. | 210/188 |
| 4,880,548 | 11/1989 | Pall et al. | 210/508 |
| 4,919,802 | 4/1990 | Katsura | 210/188 |
| 4,936,998 | 6/1990 | Nishimura et al. | 210/638 |
| 5,011,469 | 4/1991 | Buckberg et al. | 604/4 |
| 5,258,127 | 11/1993 | Gsell et al. | 210/767 |

OTHER PUBLICATIONS

R. A. Dickstein, "Reperfusion Injury: The Role of Leukocytes ", Perfusion Life, Feb. 1990, (pp. 34–38).
Breda et al., "Twenty–four Hour Lung Preservation . . . ", Heart Transplantation, vol. IV, No. 3, May 1985, (pp. 325–329).
Patterson et al., "Disposable Filter for Microemboli", JAMA, vol. 215, No. 1, Jan. 4, 1971, (pp. 76–80).
Advertisement for AUTOVENT–SP, Pall Biomedical Products Corp., copyright 1989 (two pages).
Advertisement for The Pall ECPlus Filter, Pall Biomedical Products Corp., copyright 1985, (seven pages).
Bibliography of Swank blood filters for extracorporeal circulation, GAMBRO, (eleven pages) (undated).
Advertisement for Intersept Extracorporeal Blood Filters, SURGIKOS (a Johnson & Johnson company), copyright 1976, (four pages).
Advertisement for The Pall Blood Filter for Extracorporeal Service, Pall Biomedical Corp. copyright 1976 & 1984, (six pages).

Primary Examiner—John Kim
Attorney, Agent, or Firm—Leydig, Voit & Mayer

[57] ABSTRACT

Methods, systems, and devices for processing a biological fluid including leukocytes during cardioplegia are disclosed. A method for processing a biological fluid including leukocytes comprises passing a cardioplegia fluid through a bacterial removing filter; mixing the cardioplegia fluid with the biological fluid including leukocytes to form a cardioplegia mixture; and, passing the cardioplegia mixture through a cardioplegia mixture filter assembly to produce a leukocyte-depleted cardioplegia mixture, said assembly comprising a porous medium to remove leukocytes from the cardioplegia mixture.

17 Claims, 2 Drawing Sheets

CARDIOPLEGIA FILTER AND METHOD FOR PROCESSING CARDIOPLEGIA FLUID

TECHNICAL FIELD

The invention relates to methods, devices, and systems for depleting undesirable material from fluid in a cardioplegia circuit. For example, the invention relates to the removal of leukocytes from a cardioplegia mixture in a cardioplegia circuit.

BACKGROUND OF THE INVENTION

Patients undergoing major surgery, for example, open heart surgery, typically have the functions of the heart and the lungs temporarily performed by various apparata in an external (extracorporeal) circuit. These functions may be performed by the apparatus rather than the heart and lungs of the patient since the patient's heart may be temporarily prevented from contracting or beating during the surgery. The contractions of the patient's heart may be stopped or arrested by a technique known as cardioplegia, which involves using chemical compounds, and/or cold, to arrest the contractions of the cardiac muscle, known as the myocardium.

During a typical operation requiring extracorporeal circulation, whole blood from the cardiovascular system of the patient is typically taken from the patient and collected in a container such as a venous reservoir. A wide variety of diluents, such as plasma, saline, heparin, and the like may be added to the whole blood. A pump is used to withdraw the blood from the venous reservoir and then deliver it to a gas exchanger, such as an oxygenator, which serves as an external lung. The gas exchanger may be combined with a heat exchanger to also control the temperature of the blood. Within the gas exchanger, blood is exposed to an appropriate percentage of oxygen. The exchanger may have more than one outlet, such that blood may be passed through one outlet of the exchanger and delivered to a blood filter, which removes gaseous microemboli, fat emboli, aggregates and microaggregates, and other debris. From the filter, the blood is usually returned via the arterial line directly to the vascular system of the patient.

Blood may also be passed through another outlet of the exchanger, through a different flow path involving the cardioplegia circuit. Blood passing through the cardioplegia circuit is combined with a cardioplegia fluid, such as a fluid including a high concentration of potassium. This mixture of cardioplegia fluid and blood is typically passed through a heat exchanger to cool the mixture, and then delivered to the heart, to arrest the contractions of the myocardium. After the surgery is completed, blood may be mixed with a cardioplegia fluid of lesser potassium concentration, this mixture may be warmed by passage through the heat exchanger, and the warmed mixture may be delivered to the heart before normal contractions are reinstituted.

Ancillary circuits, typically including at least one additional pump and an additional container, may be used to collect and possibly filter the blood accumulating at the operative site or elsewhere. The collected blood is delivered to the additional container, the cardiotomy reservoir, where it can be stored until the surgeon returns the blood to the patient's cardiovascular system. For example, the blood may be directed from the cardiotomy reservoir to the venous reservoir, and returned via the arterial line as described previously. By these means, the collected blood is salvaged and the need for supplemental blood replacement may be minimized.

Technological improvements involving extracorporeal circuits have generally focused on, for example, minimizing red cell damage in the arterial and cardiotomy filters, and improving the collection and salvaging efficiency of the circuits including these filters. Furthermore, since these devices are foreign to the patient's body, and may have a deleterious effect on leukocytes in the blood, some arterial filters may be designed to provide for leukocyte depletion as the blood passes repeatedly through the device. For example, during a typical operation involving a cardiac bypass, the leukocyte removal filters used in the arterial line circuit may be generally capable of removing a portion of the leukocytes in the blood recirculating in the circuit.

Leukocyte depletion may be desirable since contact between the internal surfaces of these foreign devices and the leukocytes may activate the leukocytes. This is turn may elicit an immune response and/or may result in the formation and release of a host of toxic mediators, and what is commonly referred to as oxygen-free radicals. If the leukocytes have been activated, but lack an appropriate antigenic target, the leukocytes may inflict damage to internal organs, particularly those tissues in which no blood is flowing such as the heart and lungs during certain surgical procedures.

However, none of the technological improvements noted above have addressed the need to remove deleterious matter, especially leukocytes, from fluids in a cardioplegia circuit, e.g., blood or cardioplegia fluid mixed with blood. Such removal would be especially desirable, since cardioplegia fluids and mixtures, unlike the blood returned to the body via the arterial line, are typically delivered directly to the heart. Cardioplegia fluids and mixtures are typically not a part of a recirculating system, and as a result, there is essentially only one chance to remove deleterious matter such as fat emboli, aggregates, microaggregates, leukocytes and debris from the fluid before it reaches the heart. The failure to remove deleterious matter from cardioplegia fluids and mixtures may result in "embarrassing" or "shocking" the heart by exposing it directly to this deleterious matter. Moreover, exposure to the most common leukocyte, the granulocytic neutrophil, is undesirable, since this leukocyte has been implicated as the mediator of tissue destructive events in a variety of disorders, including reperfusion injury. The commonality which pervades these pathologies is the neutrophil's ability to release a number of agents which can disrupt and destroy normal cellular function, dissolve connective tissue, and cause injury to organs. Accordingly, it would be desirable to provide a process, device and system for removing or depleting deleterious matter from cardioplegia fluids and mixtures to minimize the exposure of the heart to such matter.

These and other advantages of the present invention will be apparent from the description as set forth below.

SUMMARY OF THE INVENTION

The present invention provides a method, device and system for depleting or removing undesirable material such as deleterious matter from a fluid while passing the fluid in or through a cardioplegia circuit. In a preferred embodiment, the invention includes passing a mixture of cardioplegia fluid and blood through a porous medium, and removing leukocytes from the mixture.

Unlike the previously described protocols, which allow deleterious matter in fluid passing through a cardioplegia circuit to directly contact the heart, the present invention provides for removing or depleting deleterious matter from a fluid in a cardioplegia circuit before perfusing the heart with this fluid. Thus, the instant invention provides for minimizing the "embarrassment" or "shock" to the heart resulting from deleterious matter contacting the heart.

Additionally, since the stress of surgery may cause the heart to be more susceptible to the damaging effects of the deleterious matter, particularly leukocytes, the instant invention, by minimizing the amount of deleterious matter reaching the heart, may provide a significant benefit during extracorporeal protocols. For example, the instant invention may provide for minimizing reperfusion injury. In one embodiment, the instant invention may minimize the heart's exposure to the most common leukocyte, the granulocytic neutrophil, which has been implicated as a mediator of tissue destructive events in a variety of disorders.

An advantageous feature of the instant invention includes efficient removal of deleterious matter from the fluid during the single pass through a porous medium, since the cardioplegia circuit is typically not a recirculating system. This is in contradistinction to filtration in typical extracorporeal circuits, e.g., involving arterial line filtration of recirculated fluid wherein the filtration efficiency results from repeated passes of the fluid through the porous medium.

The present invention is especially desirable since cardioplegia protocols involve intermittent or periodic filtrations, i.e., under conditions in which there are relatively long intervals between uses of the cardioplegia circuit. Accordingly, the instant invention provides the significant advantage of single pass efficiency for each intermittent or periodic filtration.

SPECIFIC DESCRIPTION OF THE INVENTION

A method for removing deleterious matter from a cardioplegia mixture in accordance with the invention includes directing a cardioplegia mixture through a porous medium and removing deleterious matter from the cardioplegia mixture. In a preferred embodiment, removing deleterious matter includes removing a clinically or therapeutically significant amount of deleterious matter.

Cardioplegia fluid, as used herein, refers to fluids used to suspend, arrest, or modify the heart's contractions. It is intended that the invention should not be limited by the type of or constituents in the cardioplegia fluid. Typical cardioplegia fluids may be cooled or cold and/or may include one or more substances which protect the heart, particularly the myocardium, and to minimize the damaging effects caused by ischemia. Typical cardioplegia fluid ingredients or constituents include, but are not limited to at least one of potassium, a potassium-containing compound; an anti-coagulant, such as heparin; minerals, salts, sugars, nutrients, and other physiological acceptable substances. The cardioplegia fluid may be mixed with a biological fluid, e.g., a red cell containing fluid such as blood, to form, as used herein, a cardioplegia mixture.

Figure 1:
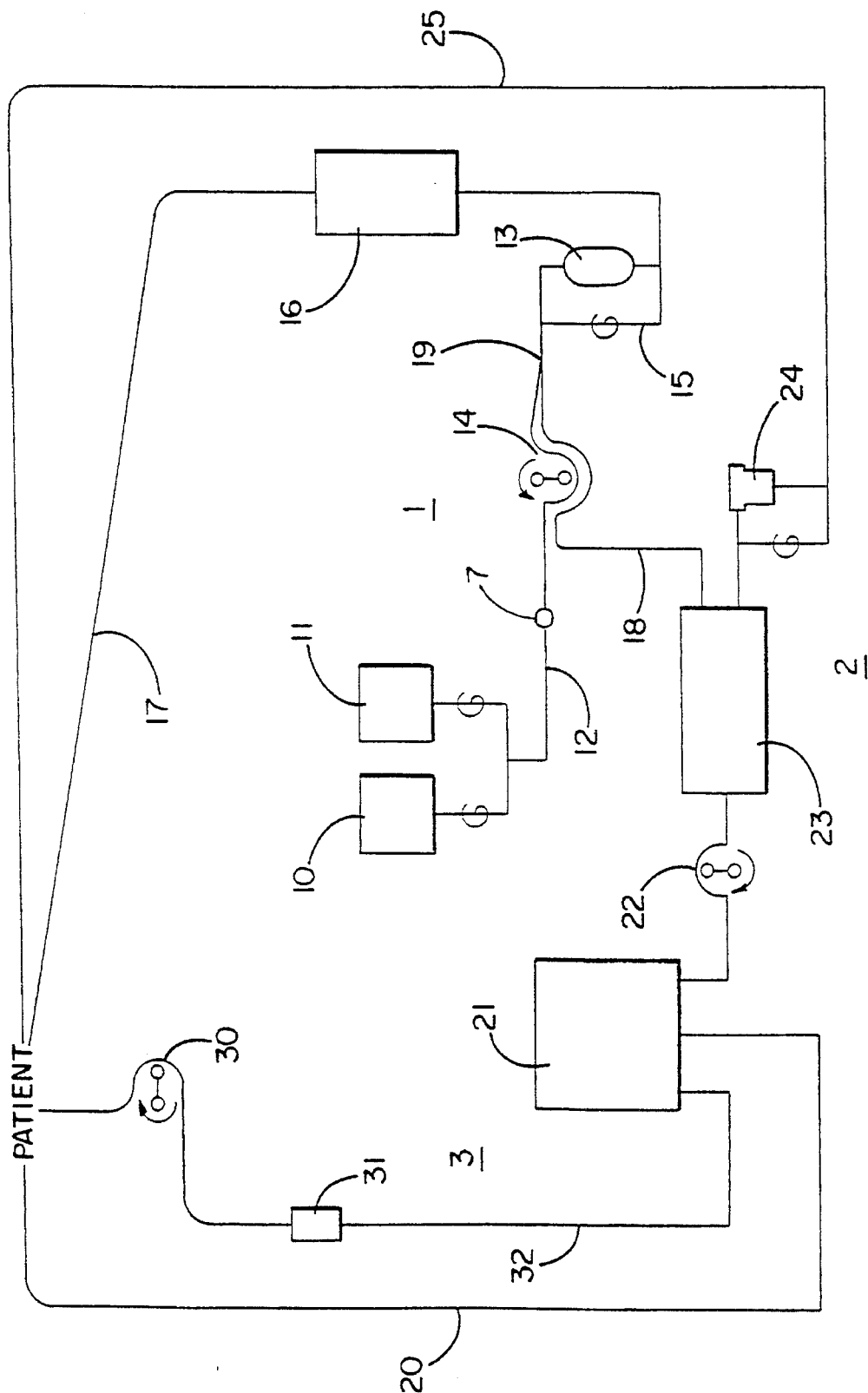
FIG. 1 is an embodiment of a cardioplegia mixture processing system according to the invention.

In an optional embodiment of the invention, cardioplegia fluid may be filtered prior to being mixed with blood. This filtration step is primarily intended to remove bacteria and the like from the cardioplegia fluid, and typically uses (as illustrated in FIG. 1) a bacterial removing filter 7 comprising a porous medium suitable for removing bacteria and the like from the cardioplegia fluid.

It is intended that the invention should not be limited by the type of deleterious or undesirable material removed or separated from the cardioplegia mixture or the biological fluid. Illustrative deleterious matter, as used herein, includes activated and non-activated leukocytes, complement (including complement factors, proteins, components, and subcomponents, as well as biologically inactive or active fragments), fat emboli, microaggregates, lipids, cells which are morphologically similar to leukocytes, cellular components, cellular components and material, and other debris. Other materials which may be removed include gas or air, stem cells, platelets, and the like. In a preferred embodiment, the method according to the invention removes greater than about 50% of the deleterious matter from the cardioplegia fluid, more preferably about 90% to about 99%, and even more preferably, greater than about 99%.

In an embodiment of the invention, the method includes directing a cardioplegia mixture through a porous medium which may include a support element, a drainage element, an element capable of removing deleterious matter from a cardioplegia fluid, a screen, and combinations thereof.

In another embodiment of the invention, the method includes removing deleterious matter from a cardioplegia mixture by passing the cardioplegia mixture through a housing; passing the cardioplegia mixture through a porous medium positioned within the housing, the porous medium comprising fibers capable of decreasing the content of deleterious matter in the cardioplegia mixture, said porous medium having a bulk density (weight per volume) in the range from about 0.03 g/cm$^3$ to about 0.25 g/cm$^3$, a fiber diameter range from about 1 μm to about 5 μm, and a porous medium surface area from about 175 cm$^2$ to about 525 cm$^2$; and removing deleterious matter from the cardioplegia mixture. In a preferred embodiment of the invention, the porous medium may have a CWST of at least about 53 dynes/cm.

Without intending to limit the invention thereby, an exemplary mode of operation for an embodiment of the invention is described by reference to an extracorporeal (EC) system used in a cardiopulmonary bypass (CPB) operation, as illustrated in FIG. 1.

In a CPB operation, the EC system commonly comprises two loops. The first loop is a cardioplegia circuit 1 involved in rendering the heart immobile and preserved or protected. The second loop is a CPB circuit 2 for bypassing the patient's heart and lungs during the operation. A CPB operation may also include a cardiotomy circuit 3 for collecting blood from the operative site. One skilled in the art will recognize that the invention as illustrated here may be reconfigured into different combinations, and may incorporate any number and combination of containers, reservoirs, conduits, flow control devices such as seals, valves, clamps, or the like; porous media, vents, flow paths, and the like. It is intended that the invention not be limited thereby.

The exemplary cardioplegia circuit 1 illustrated in FIG. 1 includes a first source of cardioplegia fluid in a container 10, typically having a high potassium content, and a second source of cardioplegia fluid in a container 11, typically having a low potassium content, in fluid communication 12 with a filter assembly 13 for removing deleterious matter from the cardioplegia mixture. The cardioplegia circuit 2 may also include a pump 14, a bypass 15, a heat exchanger 16, and a conduit 17 to establish fluid communication with the cardiovascular system of the patient. One skilled in the art will recognize that the invention as illustrated here may be reconfigured into different combinations, and may incorporate any number and combination of containers, reservoirs, conduits, flow control devices such as seals, valves, clamps, or the like; porous media, vents, flow paths, and the like. It is intended that the invention not be limited thereby.

The exemplary CPB circuit 2 includes a conduit 20 from the patient, a container such as venous reservoir 21 for holding blood, a pump 22 for passing fluid through the CPB circuit, a gas exchanger such as an oxygenator and/or a heat exchanger 23, an arterial line filter assembly 24, and a conduit 25 communicating with the cardiovascular system of the patient.

In the illustrated embodiment, the heat and gas exchanger 23 of the CPB circuit 2 is in fluid communication 18 with the cardioplegia circuit 1. In a preferred embodiment of the invention, oxygenated blood is drawn from oxygenator 23 by pump 14 and mixed with cardioplegia fluid at junction 19.

In the exemplary cardiotomy circuit 3, excess blood from the surgical site may be removed from the patient by pump 30 and delivered to a cardiotomy reservoir 31. Periodically, blood may be drawn (or flows by gravity) from the cardiotomy reservoir 31 into the venous reservoir 21, where it may be mixed with the blood in the CPB circuit.

Once the various circuits are primed, blood from the cardiovascular system of the patient may be channeled into the CPB circuit 2 through conduit 20 into venous reservoir 21. The blood is then drawn into an oxygenator/heat exchanger 23 which removes carbon dioxide from the blood and adds oxygen to the blood. Typically, the heat exchanger will warm or cool the blood as desired.

Cardioplegia fluid and the oxygenated blood may then be mixed to form a cardioplegia mixture prior to being returned to the patient. In the illustrated embodiment, pump 14 draws the oxygenated blood from the oxygenator/heat exchanger 23 and cardioplegia fluid from source container 10 or 11, the two flow paths are combined at junction 19, and a cardioplegia mixture is directed to filter assembly 13. Passing the blood, now mixed with cardioplegia fluid, through the filter assembly 13 in accordance with the invention, removes deleterious matter from the cardioplegia mixture. The treated mixture may then be passed to a device such as a heat exchanger 16, before being returned to the cardiovascular system of the patient.

In accordance with another embodiment of the invention, it may be desirable to bypass the cardioplegia filter assembly 13. In FIG. 1, an exemplary bypass includes a fluid flow path 15 which bypasses cardioplegia filter assembly 13.

The flow rate of fluid passing through a cardioplegia filter assembly 13 of the present invention can vary according to the particular use and for any given patient.

The method, system, and filter assembly according to the present invention are capable of removing a clinically or therapeutically significant amount of leukocytes and other deleterious matter from a cardioplegia mixture during typical surgical operation conditions (for example, lasting for up to about 10 hours or more). Without intending to be limited thereby, typical cardioplegia protocols may require several periodic or repeated filtrations of about 1–4 minutes duration.

In accordance with the invention, the deleterious matter content of a cardioplegia mixture is depleted. This generally means removing a therapeutically or clinically significant amount of deleterious matter from a cardioplegia mixture or biological fluid. "Therapeutically or clinically significant amount" refers to an amount necessary to produce a beneficial effect on the patient or animal receiving the fluid. Such a beneficial effect may be, for example, lessening reperfusion injury. A therapeutically or clinically significant amount can vary depending on the intended use and/or from patient to patient. Removal of a therapeutically or clinically significant amount can be and is routinely determined by a doctor or technician for treating a certain condition or disease as it pertains to the specific patient or animal, and as it pertains to the particular application.

As noted above, the cardioplegia circuit may be pre-primed or may be primed as a preliminary step in the cardioplegia fluid processing.

A method of the present invention may be used in any procedure, therapy, operation, or environment in which the removal of deleterious matter, particularly leukocytes, is desirable or beneficial. Because leukocytes have the potential for becoming activated upon contact with almost anything ex-vivo, many applications exist for the use of the method, system, and filter assemblies of the present invention in reducing the number of activated leukocytes and amount of other deleterious matter. While the filter assembly of the present invention is particularly suited for treating reperfusion-induced injury and/or achieving leukocyte content equilibrium in an extracorporeal system, including a cardioplegia circuit, one skilled in the art will recognize other contexts in which removal of leukocytes and other deleterious matter in a liquid is desirable.

A system in accordance with the invention may include a source of biological fluid; at least one source of cardioplegia fluid; and a filter assembly in fluid communication with the source of biological fluid and the source of cardioplegia fluid, said filter assembly being capable of removing deleterious matter from the mixture of cardioplegia fluid and biological fluid. In a preferred embodiment of the invention, the system is a sterile system.

One skilled in the art will recognize that the system as described may be configured into different combinations, and may incorporate any number and combination of containers, reservoirs, conduits, flow control devices such as seals, valves, clamps, or the like; porous media, vents, flow paths, and the like. It is intended that the invention should not be limited thereby.

Figure 2:
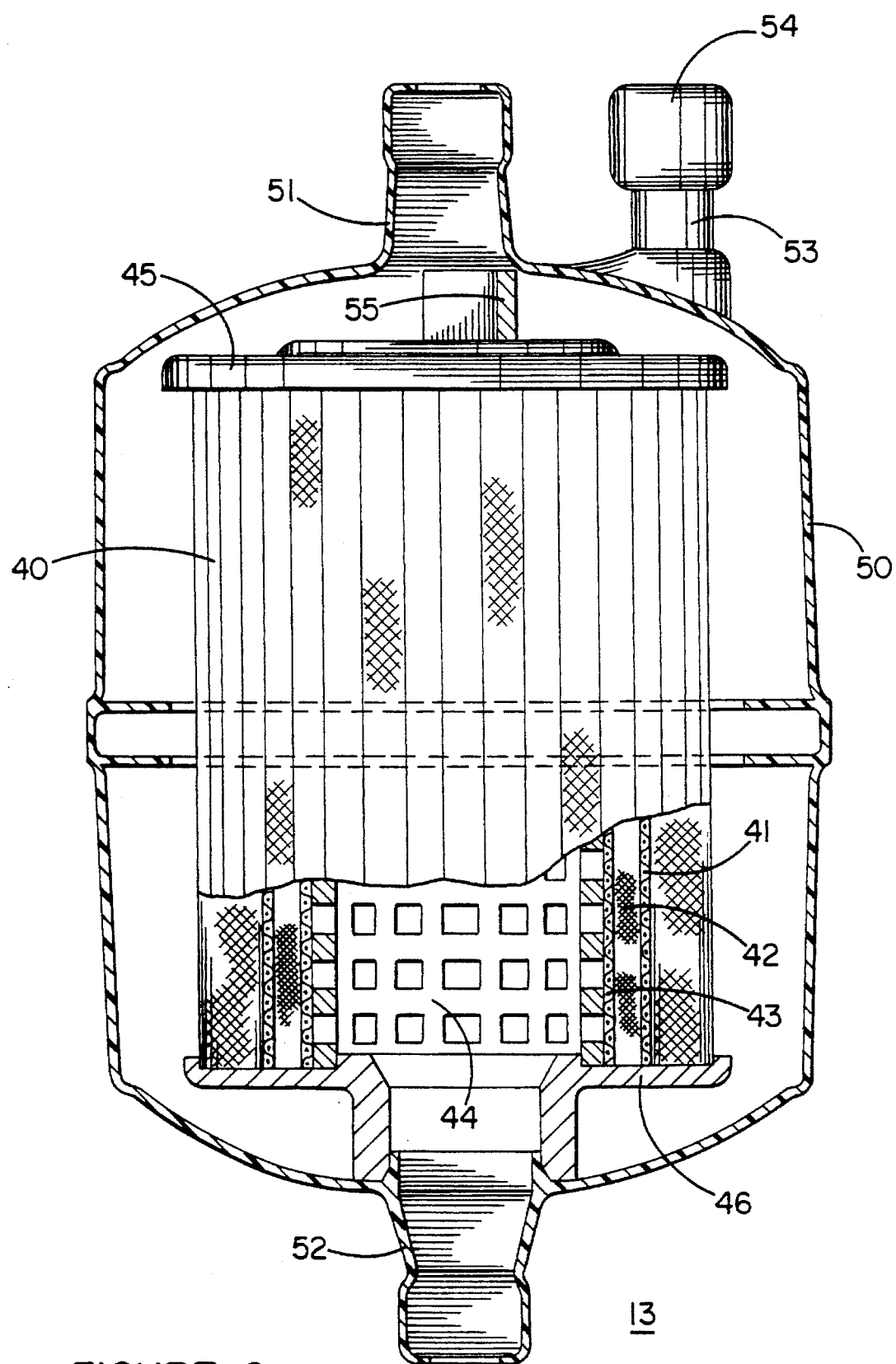
FIG. 2 is a cross section of a typical cardioplegia filter assembly.

In accordance with an embodiment of the invention, a cardioplegia filter assembly may be positioned in any location in cardioplegia circuit 2, including either prior to pump 14, or after heat exchanger 16. The preferred position of the cardioplegia filter assembly is shown in FIG. 2.

A filter assembly in accordance with the present invention comprises a housing having an inlet and an outlet; a fluid flow path between the inlet and the outlet; and a porous medium disposed in the housing across the fluid flow path and capable of depleting or removing deleterious matter from a cardioplegia mixture or biological fluid. In a preferred embodiment, the porous medium is capable of removing a therapeutically or clinically significant amount of deleterious matter from a cardioplegia mixture.

In accordance with the invention, the filter assembly 13 includes a housing 50 having an inlet 51 and an outlet 52 defining a fluid flow path between the inlet and the outlet, and having a porous medium 40 disposed across the fluid flow path. The filter assembly may also include a vent 42, having a removable or puncturable cap 43, and/or a bypass fluid flow path 15 communicating with the inlet 51 and the outlet 52 to allow cardioplegia mixture to pass around the filter assembly without passing through the porous medium. A variety of suitable vents are known in the art.

In accordance with the invention, the filter assembly includes a porous medium suitable for removing deleterious matter from a cardioplegia mixture or biological fluid. The porous medium may include multiple layers and/or elements. In an embodiment of the invention, the porous medium includes a porous removal element capable of removing deleterious matter from a cardioplegia mixture, said porous element preferably comprising fibers, more preferably synthetic, polymeric fibers. If a fibrous element is used, the fibers may be untreated, or they may be treated either before or after forming the fibrous lay-up. It is preferred to modify the fiber surface before forming the fibrous lay-up because a more cohesive, stronger product is obtained after hot compression to form an integral element.

The porous medium may also include at least one element or layer to provide support, better drainage, and/or improved flow characteristics, such as more uniform flow distribution. Preferably, the porous medium includes at least one drainage element, at least one support element, at least one screen element, a core element, or combinations thereof. While the porous medium may take any of a number of forms, in a preferred embodiment, the porous medium is pleated or corrugated. For example, the pleated porous medium may have longitudinally extending pleats having peaks.

In an embodiment of the invention, the porous medium may include a bulk density (weight per volume) in the range from about 0.03 g/cm$^3$ to about 0.25 g/cm$^3$, a fiber diameter range from about 1 µm to about 5 µm, and a porous medium surface area from about 175 cm$^2$ to about 525 cm$^2$, preferably from about 300 cm$^2$ to about 400 cm$^2$.

As shown in FIG. 2, an exemplary embodiment of a filter assembly 13 according to the invention has a hollow, generally cylindrical configuration and comprises a porous medium 40 which may include a support and/or drainage element 41, a removal element 42, and a porous element or screen 43. The porous medium may also include a perforated core 44, an upper blind end cap 45, and a lower open end cap 46. The porous medium 40 is preferably disposed within the housing 50 so that the interior of the porous medium 40 communicates with a centrally located outlet 52.

The porous element or screen 43, which preferably has a pore size no greater than about 40 microns, is disposed coaxially adjacent to the downstream surface of the removal element 42, e.g., around the interior of the removal element. The screen 43 may be fashioned from any compatible porous membrane or woven or non-woven material, including a mesh or a screen. The screen 43 serves principally as a final filter to remove, for example, any debris such as aggregates which escape the removal element or form at the downstream portion of the removal element.

The perforated core 44 is disposed within and adjacent to the interior of the screen 43 and serves principally to support the removal element 42 and the screen 43 against the differential pressure across the porous medium 40. Consequently, the perforated core 44 may be fashioned from any suitably rigid material including a metal such as stainless steel or a rigid polymer such as polyolefin, polyester, or polyacrylate.

The end caps 45, 46 serve to direct the liquid radially outside/in through the porous medium 40. Both end caps 45, 46 may be fashioned from any suitably impervious material, such as a metallic or polymeric material, preferably a polymer such as polypropylene, which is compatible with the fluid to be filtered; the end caps are fixed to the respective ends of the removal element 42, the screen 43, and the perforated core 44. Alternatively, the lower ends of the removal element, the screen, and the perforated core may be fixed directly to the bottom wall of the body, eliminating the need for a lower end cap. The end caps 45 and 46 may be secured to the ends of the porous medium by any suitable means, including but not limited to, a bonding agent, melt bonding, spin bonding, or sonic welding. The ends of the hollow core 44 may be secured to the two end caps 45 and 46 by similar means.

A blind end cap 45 and an open end cap 46 may be fitted over the two ends of the porous medium to direct fluid through the porous medium. Alternatively, both end caps can be open or can include connectors to link a stack of porous media. Alternatively, the porous medium may be designed for inside/out flow. The screen may then be disposed around the exterior of the removal element, the upper end cap may be an open end cap, and the lower end cap may be a blind end cap. The core may be omitted but a cage disposed coaxially around the screen to support the porous medium against the pressure drop may be added. Of course, the housing would be rearranged to permit the inlet to communicate with the interior of the porous medium and the outlet to communicate with the exterior of the porous medium.

The filter assembly may configured in a variety of ways and/or according to an intended use. For example, the filter assembly may provide for additional flow paths for the cardioplegia mixture and/or gas. Accordingly, the filter assembly may provide for a gas flow path, e.g., wherein the filter assembly includes a least one vent such as a gas outlet for the separation or removal of gas from the cardioplegia mixture and/or the filter assembly.

In a preferred embodiment, as exemplified in FIG. 2, a vent 53 may be asymmetrically located near the inlet, which provides for more efficient venting, e.g., by creating a short escape path for potentially large volumes of entrained gas.

In an alternative embodiment of the invention, a deflector or baffle 55, preferably a semicylindrical deflector, may extend from the housing 50 near the inlet 51 to the end cap 45. The deflector 55 may be variously configured, and is intended to improve venting efficiency, e.g., by directing microbubbles around the periphery of the porous medium 40 and toward the vent 53; for holding the porous medium 40 axially in the housing 50; and for deflecting incoming fluid away from the vent 53.

The filter assembly may be configured in a variety of ways in accordance with the invention. For example, the hold-up volume of the filter assembly is preferably in the range from about 100 ml to about 400 ml, even more preferably, from about 175 ml to about 225 ml. Furthermore, the filter assembly may include a hollow porous medium which may have a cylindrical shape and may be disposed in the housing to filter liquid flowing laterally or radially through the filter element. For example, to filter liquid flowing inside/out through the porous medium, the inlet and outlet of the filter assembly would be arranged to respectively communicate with the interior and exterior of the hollow porous medium.

In the illustrated embodiment, the filter assembly is arranged to filter liquid flowing outside/in through the porous medium. This arrangement is preferred because it provides a porous medium with a large surface area in a compact housing.

Any housing of suitable shape to provide an inlet and an outlet for liquid and a space for a porous medium disposed between the inlet and outlet can be employed. A preferred embodiment of the filter assembly comprises a generally cylindrical housing 50 having an inlet 51 and an outlet 52, as shown in FIG. 2. Housings can be designed to accept a variety of shapes of filter assemblies. For example, a square or octagon shaped housing and other possible forms designed to accommodate a similarly shaped porous medium would in principle all be functional, provided that adequate flow area is provided by the porous medium. These shapes are within the scope of the claimed invention. Any housing of suitable configuration to reliably contain the liquid and define a liquid flow path through the porous medium can be employed.

The housing may be fabricated from any sufficiently rigid, impervious material which is compatible with the biological fluid. For example, the housing may be fabricated from a metal, such as stainless steel, or from a polymer. In a preferred embodiment, the housing is fabricated from a plastic material, such as polystyrene, polycarbonate, or polypropylene. In addition, all of the surfaces of the housing which contact the liquid are preferably liquophilic, i.e., readily wettable by the fluid. For example, the internal surfaces of the housing 50 may be treated to achieve a high degree of liquophilicity, e.g., by surface graft co-polymerization of hydroxyl functional monomers or by subjecting the internal surfaces to gas plasma treatment. These liquophilic internal surfaces then readily facilitate the release of gas bubbles during the preparation and priming operation. A method of reducing the adhesion of bubbles in medical equipment is disclosed in U.S. Pat. No. 4,861,617.

In accordance with one aspect of the invention, the porous medium may be fashioned to decrease the leukocyte content of a cardioplegia mixture or a biological fluid which is passed through the porous medium. The porous medium may be fashioned in a variety of ways to effectively remove the leukocytes, as well as other deleterious matter from the fluid. In a preferred embodiment, the porous medium may be any medium or combination of media which maintain leukocyte removal without clogging. For example, the porous medium preferably comprises a fibrous structure made from any material compatible with the liquid and may be untreated or may be treated in a variety of ways to make the porous medium even more effective. The fibers may be bonded, fused, or otherwise fixed to one another or they may simply be mechanically entwined. In another embodiment, the fiber diameter and/or void spaces may vary in a continuous or stepwise manner. In another embodiment of the invention, the pore rating of the porous medium may be up to about 15 µm, preferably about 4 µm to about 8 µm. In a less desirable embodiment, the porous medium may include a graded pore structure over at least a substantial radial portion of the porous medium.

Further, the porous medium may be configured as a flat sheet, a corrugated or pleated member, and preferably also includes structures such as end caps, edge seals, a cage, a core, or a wrap.

In a preferred embodiment, the porous medium also may include a downstream screen, preferably about a 40 micron screen, suitable for removing debris greater than about 40 microns.

The removal element 42 may preferably be configured as a mass of non-woven, synthetic, polymeric fibers. The fibers may be bonded, fused, or otherwise fixed to one another, or they may be substantially free of fiber-to-fiber bonding and secured to each other by mechanical entanglement or intertwining. The term "fibers" includes filaments, and the term "substantially free of fiber-to-fiber bonding", as used herein, refers to the characteristics of the fibers making up the removal element 42. Thus, although the removal element 42 may display random fiber-to-fiber bonding, such bonding would not contribute in any material way to the structural integrity of the filter element. Exemplary removal elements are described in U.S. Pat. Nos. 4,925,572; 4,923,620; and 5,229,012. Exemplary removal elements may have a thickness from about 0.03 inch to about 0.11 inch, preferably from about 0.06 inch to about 0.08 inch; may be multi-layered, preferably having 2 to about 10 layers, more preferably about 3 to 5 layers; and each of the removal element layers may have a weight/area of about 2.5 g/ft$^2$ to about 8.0 g/ft$^2$, preferably about 4.0 g/ft$^2$ to about 6.0 g/ft$^2$. For example, a typical porous medium according to the invention may have a weight per area of about 10 g/ft$^2$ to about 30 g/ft$^2$, preferably 17 g/ft$^2$ to about 23 g/ft$^2$.

Polymeric materials particularly well suited for the removal element include, but are not limited to thermoplastics such as the polyolefins, particularly polypropylene and polymethylpentene; polyamides, particularly nylon 6, nylon 610, nylon 10, nylon 11, nylon 12; and polyesters, particularly polybutylene terephthalate and polyethylene terephthalate. Other suitable, but less preferred, polymers are addition polymers such as polyvinyl fluoride, polyvinylidene fluoride and their copolymers. The preferred material is polybutylene terephthalate.

In the illustrated embodiment, the annular thickness of the pleated structure of a fibrous medium is preferably in the range from 0.1 to about 3 inches (0.25 cm to 7.62 cm), more preferably in the range from about 0.2 to about 0.8 inch (0.51 to 2.0 cm), and most preferably in the range from about 0.3 to about 0.6 inch (0.76 to 1.52 cm). The outer diameter of the fibrous medium is preferably less than about 8.5 inches (21.6 cm), more preferably less than about 3 inches (7.62 cm). The height of the pleated structure is preferably up to about 5.5 inches (14 cm), more preferably about 2.5 inches (6.4 cm). The hold up volume of the filter assembly is typically up to about 400 cubic centimeters, more preferably, 100 ccs to 250 ccs.

Although the fibers of the porous medium may remain untreated, they are preferably treated to make them even more effective for removing leukocytes and other deleterious matter. For example, the fibers may be surface modified to increase the critical wetting surface tension (CWST) of the fibers, in addition to affecting other characteristics of the fibers. Exemplary techniques for determining and modifying the CWST include those disclosed in U.S. Pat. No. 4,880,548. As noted above, the CWST of the porous medium is preferably above about 53 dynes/cm, more preferably between about 60 dynes/cm and about 70 dynes/cm.

Surface characteristics of a fiber can be modified by a number of methods, for example, by chemical reaction including wet or dry oxidation, by coating the surface by depositing a polymer thereon, and by grafting reactions which are activated by exposure to an energy source such as heat, a Van der Graff generator, ultraviolet light, gas plasma, or to various other forms of radiation.

The benefits conferred by modifying fibers to CWST values higher than the natural CWST of synthetic fibers include:

(a) The time to achieve priming is significantly reduced.
 (b) Fibrous media treated to convert the fiber surfaces to a particular range of CWST perform better with respect to efficiency and resistance to clogging than do fibrous media with CWST values outside of those ranges.
 (c) The detrimental effects associated with non-wetting, e.g., uneven flow through the porous medium, are avoided.

(d) Devices made using unmodified synthetic fibers are recommended to be flushed with saline prior to use. This operation is sometimes undesirable since it causes blood loss due to hold-up within the complex tubing arrangement required, adds to cost, operation time, and operation complexity, and increases the probability that sterility may be lost.

A filter assembly of the present invention may be used in any procedure which requires perfusion, the passage of blood or other fluid through the blood or lymph vessels of the body, using blood or other fluid which has been exposed to anything ex-vivo (and therefore potentially containing activated leukocytes).

EXAMPLES

Example 1

A cardioplegia filter assembly in accordance with the invention was produced as follows: polybutylene terephthalate (PBT) was formed into fibers by melt blowing, i.e., exposing molten PBT resin to a high velocity stream of gas, until 20.8 gm/ft$^2$ of fibers having an average diameter of 2.4 microns was obtained. Four layers, having a total thickness of 0.070 inch and having a quantity of fibers corresponding to 5.2 g/ft$^2$/layer, were formed and combined. This pack was then combined with a single layer of 40 micron opening woven polyester mesh. These five layers were pleated together with an extruded polypropylene mesh having a thickness of 0.02 inch (0.05 cm) and openings of about 0.06 inch (0.15 cm) by 0.06 inch (0.15 cm). The bulk density of the porous medium was 0.126 g/cm$^3$. The pleats were formed using conventional pleating equipment having heated platens to maintain the pleated structure to form a structure having about 5 pleats per inch and a height of about 0.4 inch. The surface area of the porous medium was 54 in$^2$. The CWST of the porous medium was 65 dynes/cm, and had a pore rating of about 5 μm.

The pleated media assembly was cut to a length of 2.3 inches and a diameter of 2.1 inches, i.e., about 30 pleats. The assembly was formed into a cylindrical structure and the ends were sealed using a conventional heat sealer. A polypropylene core was placed inside the pleated cylinder, and polypropylene end caps were heat welded to the ends of the cylinder.

The filter assembly was then assembled into a housing in preparation for testing for leukocyte removal from blood.

Example 2

This Example illustrates the use of the cardioplegia filter assembly of Example 1 in an cardioplegia circuit for the removal of leukocytes from a cardioplegia mixture. This test was designed to expose a cardioplegia mixture to the conditions typical of those encountered during cardio-pulmonary bypass surgery: a cardioplegia circuit having a source of high potassium cardioplegia fluid, a source of low potassium cardioplegia fluid, a pump, a junction for combining blood with the cardioplegia fluid, and the cardioplegia filter assembly described in Example 1. Blood samples were taken and the differential pressure across the filter was measured at various times during the test.

Two units of type-matched CPD whole blood to which a heparin anti-coagulant had been added were placed in the container. After the filter and circuit were primed, blood in the container was mixed with cardioplegia fluid at a flow rate of 500 cc per minute.

From samples of blood taken at various intervals during the test, it was found that the total leukocyte removal (neutrophils and lymphocytes), using a treated porous medium produced as described in Example 1, was greater than 99%. The pressure differential was less than 2.5 psi throughout the test.

These results illustrate the ability of the porous medium of the present invention to effectively remove leukocytes from a cardioplegia mixture while maintaining a desirably low pressure drop.

While the invention has been described in some detail by way of illustration and example, it should be understood that the invention is susceptible to various modifications and alternative forms, and is not restricted to the specific embodiments set forth. It should be understood that these specific embodiments are not intended to limit the invention but, on the contrary, the intention is to cover all modifications, equivalents, and alternatives falling within the spirit and scope of the invention.

We claim:

1. A method for processing a biological fluid including leukocytes comprising:

passing a cardioplegia fluid through a bacterial removing filter;

mixing the cardioplegia fluid with the biological fluid including leukocytes to form a cardioplegia mixture; and, passing the cardioplegia mixture through a cardioplegia mixture filter assembly to produce a leukocyte-depleted cardioplegia mixture, said assembly comprising a porous medium to remove leukocytes from the cardioplegia mixture, said porous medium having an upstream surface and a downstream surface.

2. The method of claim 1 further comprising directing cardioplegia mixture in a fluid flow path which bypasses the porous medium.

3. The method of claim 1 comprising passing a cardioplegia fluid including potassium through the bacterial removing filter.

4. The method of claim 1 further comprising passing the leukocyte-depleted cardioplegia mixture from the cardioplegia mixture system through a heat exchanger.

5. The method of. claim 4 further comprising passing the leukocyte-depleted cardioplegia mixture to the heart of a patient.

6. The method of claim 5 wherein the leukocyte-depleted cardioplegia mixture passed to the patient is depleted of greater than 90% of the leukocytes in the cardioplegia mixture that were present at the upstream surface of the porous medium.

7. A system for use in a cardioplegia circuit comprising:

at least one container for holding a cardioplegia fluid;

a bacterial removing filter for use with at least one cardioplegia fluid, said filter being located downstream of said container and in fluid communication therewith;

a junction for use in mixing cardioplegia fluid with biological fluid including leukocytes, to form a cardioplegia mixture, said junction being located downstream of said bacterial removing filter and in fluid communication therewith, wherein the bacterial removing filter is interposed between the container and the function; and, a filter assembly for processing a cardioplegia mixture, said assembly comprising a housing having an inlet and an outlet and defining a fluid flow path between the inlet and the outlet; said assembly including a porous medium positioned inside the housing across the fluid flow path and capable of depleting leukocytes from the cardioplegia mixture, said assembly being located downstream of the junction for mixing cardioplegia fluid with biological fluid and in fluid communication therewith, wherein the junction is interposed between the filter assembly and the bacterial removing filter.

8. The system of claim 7 further comprising a bypass fluid flow path communicating with the inlet and the outlet.

9. The system of claim 7 wherein the porous medium is a pleated porous medium.

10. The system of claim 7 further comprising an additional container for holding a cardioplegia fluid.

11. The system of claim 7 wherein the porous medium includes at least one support element, a drainage element, and an element capable of removing leukocytes from a cardioplegia mixture, and a screen.

12. The system of claim 11 wherein the porous medium comprises a bulk density in the range from about 0.03 g/cm$^3$ to about 0.25 g/cm$^3$, and a fiber diameter range from about 1 μm to about 5 μm.

13. The system of claim 12 further comprising a porous medium having a surface area from about 175 cm$^2$ to about 525 cm$^2$.

14. The system of claim 11 wherein the element capable of removing leukocytes from a cardioplegia mixture includes at least two layers and each of the layers have a weight to area value of about 2.5 g/ft$^2$ to about 8.0 g/ft$^2$.

15. The system of claim 11 wherein the element capable of removing leukocytes from a cardioplegia mixture has a weight per area range from about 10 g/ft$^2$ to about 30 g/ft$^2$.

16. A method for reducing shock to the heart in a cardioplegia circuit comprising:

passing biological fluid including leukocytes from a venous reservior through an oxygenator/heat exchanger;

passing a cardioplegia fluid including potassium through a bacterial removing filter;

mixing the biological fluid with the cardioplegia fluid to form a cardioplegia mixture;

passing the cardioplegia mixture through a cardioplegia mixture system to produce a leukocyte-depleted cardioplegia mixture, said assembly comprising a porous medium to remove leukocytes from the cardioplegia mixture; and, passing the leukocyte-depleted cardioplegia mixture to the heart of a patient.

17. The method of claim 16 wherein the leukocyte-depleted cardioplegia mixture passed to the heart of the patient is depleted of greater than 90% of the leukocytes in a single pass through the porous medium.

* * * * *